(12) United States Patent
Zhi

(10) Patent No.: US 10,000,522 B2
(45) Date of Patent: Jun. 19, 2018

(54) DERIVATIVES OF URIDINE 5'-CYCLOPHOSPHATE USEFUL TO TREAT HEPATITIS C VIRAL INFECTIONS

(71) Applicant: Ligand Pharmaceuticals Incorporated, La Jolla, CA (US)

(72) Inventor: Lin Zhi, San Diego, CA (US)

(73) Assignee: Ligand Pharmaceuticals Incorporated, La Jolla, CA (US)

( * ) Notice: Subject to any disclaimer, the term of this patent is extended or adjusted under 35 U.S.C. 154(b) by 0 days. days.

(21) Appl. No.: 15/590,813

(22) Filed: May 9, 2017

(65) Prior Publication Data

US 2017/0334942 A1 Nov. 23, 2017

Related U.S. Application Data

(63) Continuation of application No. 15/034,757, filed as application No. PCT/US2014/066456 on Nov. 19, 2014, now Pat. No. 9,676,809.

(60) Provisional application No. 61/907,600, filed on Nov. 22, 2013.

(51) Int. Cl.
  *C07H 19/10* (2006.01)
  *C07H 19/11* (2006.01)
(52) U.S. Cl.
  CPC ............. *C07H 19/10* (2013.01); *C07H 19/11* (2013.01)

(58) Field of Classification Search
  None
  See application file for complete search history.

(56) References Cited

U.S. PATENT DOCUMENTS

| | | |
|---|---|---|
| 7,666,855 B2 | 2/2010 | Reddy |
| 8,063,025 B2 | 11/2011 | Hecker |
| 9,676,809 B2 * | 6/2017 | Zhi ........................ C07H 19/10 |

FOREIGN PATENT DOCUMENTS

| WO | WO 2009/073506 | 6/2009 |
|---|---|---|
| WO | WO 2013/106344 | 7/2013 |

OTHER PUBLICATIONS

Meier, et al, Synthesis, Hydrolysis and Anti-EBV Activity of a Series of 3'-Modified cyclo Sal-BVDUMP Pronucleotides, Nucleosides, Nucleotides & Nucleic Acids 20(4-7):307-314 (2001).

* cited by examiner

*Primary Examiner* — Traviss C McIntosh, III
(74) *Attorney, Agent, or Firm* — Knobbe, Martens, Olson & Bear LLP

(57) ABSTRACT

Some embodiments of the present invention include nucleoside 5'-monophosphate derivative compounds, their preparation and their uses. In some embodiments, such compounds are useful to treat hepatitis C viral infections.

20 Claims, No Drawings

DERIVATIVES OF URIDINE 5'-CYCLOPHOSPHATE USEFUL TO TREAT HEPATITIS C VIRAL INFECTIONS

RELATED APPLICATIONS

This application is a continuation of U.S. application Ser. No. 15/034,757 filed May 5, 2016 which is the U.S. National Phase of International Application No. PCT/US2014/066456 filed on Nov. 19, 2014 and was published in English as WO2015/077368 on May 29, 2015 which claims the benefit of U.S. Provisional Application No. 61/907,600 entitled "LIVER-TARGETING NUCLEOSIDE PRODRUG COMPOUNDS AND USES THEREOF" filed Nov. 22, 2013, which are each incorporated by reference herein in its entirety.

FIELD OF THE INVENTION

The disclosure is in the field of medicinal compounds, medicinal compositions, as well as process for their preparation and methods of their use. Some embodiments of the present invention include nucleoside 5'-monophosphate derivative compounds, their preparation and their uses. In some embodiments, such compounds are useful to treat hepatitis C viral infections.

BACKGROUND OF THE INVENTION

Hepatitis C is a viral disease that causes inflammation of the liver that may lead to cirrhosis, primary liver cancer and other long-term complications. Synthetic nucleosides are a well-recognized class of compounds shown to be effective against a variety of viral infections, including hepatitis B, HIV, and herpes. Several synthetic nucleosides are reported to inhibit hepatitis C virus (HCV) replication, including ribavirin, which currently is marketed as a drug combination with various forms of interferon. The nucleosides are prodrugs that need to be converted to the biologically active corresponding nucleoside 5'-triphosphate (NTP) in a sequential three-step activation process inside cells by various intracellular kinases. The first step, i.e. conversion of the nucleoside to the 5'-monophosphate (NMP), is generally the slowest step and involves a nucleoside kinase, which is encoded by either the virus or host. Conversion of the NMP to the NTP is generally catalyzed by host nucleotide kinases. The NTP interferes with viral replication through inhibition of HCV NS5B polymerase, an RNA-dependent RNA polymerase (RdRp), and/or via incorporation into a growing strand of RNA followed by chain termination. Since the rate and efficiency of NTP formation are dependent upon structure of each nucleoside, virus genetic make-up, and host cell environment, antiviral activity of a synthetic nucleoside is determined by intrinsic activity of the NTP, NTP half-life, and the nucleoside activation efficiency in a cell.

Natural nucleosides and nucleotides are building blocks of RNA and DNA, and are essential elements for life. Among others they play important roles in DNA replication, cell signaling, and metabolism. Synthetic nucleosides are close analogs of natural nucleosides and are used as antiviral and anticancer agents by taking advantages of the RNA/DNA chain termination property. As a result, identification of compounds that selectively inhibit viral or cancer cell proliferation from normal cells can be challenging.

Nucleosides are hydrophobic molecules with multiple polar functional groups that often contribute to poor oral bioavailability due to poor permeability at gastrointestinal tract, although certain nucleosides such as ribavirin can be moderately absorbed at gastrointestinal tract via transporters. Most synthetic nucleoside analog drugs need a lipophilic moiety to mask the polar functional groups, which adds another layer of prodrug activation of a drug.

The diverse biological functions of nucleosides and the complexity of multiple layers cell-dependent prodrug activation make the development of nucleoside analogs for HCV treatment a substantial challenge. First generation nucleoside-based HCV NS5B polymerase inhibitors were simple ester prodrugs designed to provide oral bioavailability. For example, NM283, R1626, and R7128 were orally available nucleoside prodrugs but failed to adequately address other challenges of nucleoside-based prodrugs. Both R1626 and NM283 demonstrated clinical efficacy in HCV infected patients in phase II clinical trials but also encountered safety issues presumably due to non-discriminate distribution and activation of the nucleosides. R7128 faced a different challenge in clinic where its efficacy is significantly compromised due to the slow conversion of the nucleoside to the active nucleotides.

Second generation nucleoside-based prodrugs of HCV NS5B polymerase inhibitors were designed to deliver nucleoside 5'-monophosphates to improve the efficiency of nucleoside activation in the cells.

Certain other phosphate prodrugs are disclosed in U.S. Pat. Nos. 8,063,025, 7,666,855, and PCT Pub. No. WO2009/073506.

SUMMARY OF THE INVENTION

Some embodiments of the compounds, compositions, and methods provided herein include a compound of Formula I:

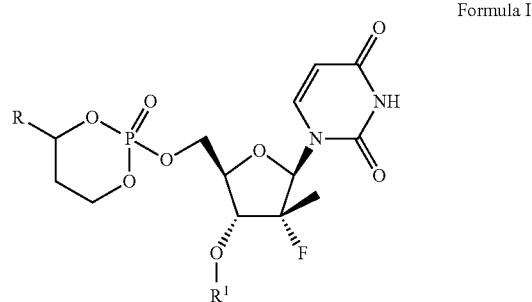

Formula I wherein:
R is an optionally substituted phenyl or an optionally substituted pyridyl;
$R^1$ is selected from the group of a $C_1$-$C_6$ alkyl, a $C_1$-$C_6$ haloalkyl, a $C_1$-$C_6$ heteroalkyl, a $C_1$-$C_6$ acyl, a $C_1$-$C_6$ haloacyl, a $C_1$-$C_6$ heteroacyl, and a $C_1$-$C_6$ haloheteroacyl; provided that $R^1$ is not propionyl;
or a pharmaceutically acceptable salt thereof.

In some embodiments, R is selected from the group consisting of:

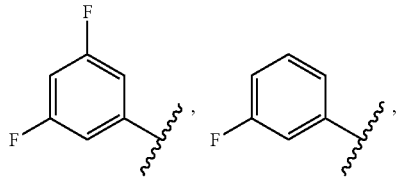

In some embodiments, R is selected from the group consisting of

In some embodiments, $R^1$ is selected from the group of a $C_1$-$C_6$ alkyl, a $C_1$-$C_6$ heteroalkyl.

In some embodiments, $R^1$ is a $C_1$-$C_6$ acyl; provided that $R^1$ is not propionyl.

In some embodiments, $R^1$ is selected from the group of a $C_1$-$C_6$ haloacyl, a $C_1$-$C_6$ heteroacyl, and a $C_1$-$C_6$ haloheteroacyl.

In some embodiments, $R^1$ is selected from the group consisting of —C(=O)C(NH$_2$)R$^2$, —CH$_2$R$^3$, —C(=O)CH$_3$, —C(=O)CF$_3$, —C(=O)CH$_2$CF$_3$, —C(=O)CH$_2$OCH$_3$, and —C(=O)OCH$_2$CH$_3$, wherein $R^2$ is alkyl; $R^3$ is selected from —OH, —CH$_3$, or —O—C(=O)CH$_3$.

In some embodiments, Formula I is selected from the group consisting of

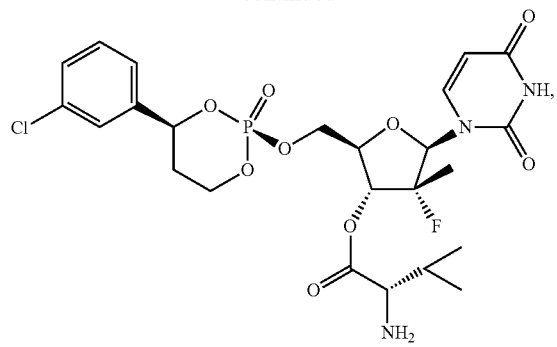
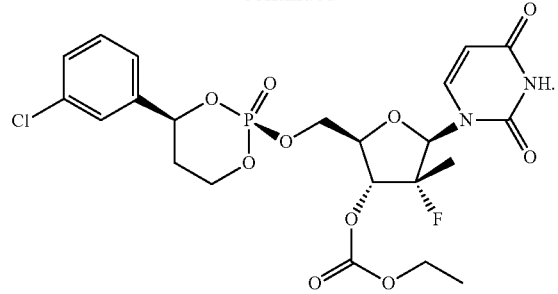

Some embodiments of the compounds, compositions, and methods provided herein include a pharmaceutical composition comprising any of the compounds provided herein and a pharmaceutically acceptable excipient.

Some embodiments of the compounds, compositions, and methods provided herein include a method of treating a viral liver infection in a subject comprising administering an effective amount of any of the compounds provided herein to a subject in need thereof.

Some embodiments also include administering an effective amount of additional therapeutic agent to the subject in need thereof.

In some embodiments, the additional therapeutic agent is selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α.

In some embodiments, the additional therapeutic agent comprises interferon-α or pegylated interferon-α.

In some embodiments, the additional therapeutic agent comprises a direct-acting antiviral agent (DAA) or a host-targeting antiviral (HTA). In some embodiments, the direct-acting antiviral agent is selected from the group consisting of an inhibitor of HCV protease, an inhibitor of HCV NS5A replication complex, a nucleoside-based inhibitor of HCV NS5B polymerase, a non-nucleoside inhibitor of HCV NS5B polymerase, and an inhibitor of HCV helicase.

In some embodiments, the viral infection comprises hepatitis C.

In some embodiments, the subject is a mammal.

In some embodiments, the subject is a human.

Some embodiments of the compounds, compositions, and methods provided herein include method of inhibiting viral replication in a cell comprising contacting the cell with any one of the compounds provided herein.

In some embodiments, the viral replication is RNA-dependent.

In some embodiments, the viral replication is HCV replication.

Some embodiments also include contacting the cell with an additional antiviral agent.

In some embodiments, the additional antiviral agent is selected from the group consisting of thymosin alpha-1, interferon-λ, an inhibitor of HCV protease, an inhibitor of HCV NS5A replication complex, an inhibitor of HCV NS5B polymerase, a cyclophilin inhibitor, an inhibitor of inosine monophosphate dehydrogenase, ribavirin, interferon-α, and pegylated interferon-α.

In some embodiments, the additional therapeutic agent comprises interferon-α or pegylated interferon-α.

In some embodiments, the cell is in vivo.

In some embodiments, the cell is ex vivo.
In some embodiments, the cell is a hepatocyte.
In some embodiments, the cell is mammalian.
In some embodiments, the cell is human.

Some embodiments of the compounds, compositions, and methods provided herein include the use of any one of the compounds provided herein for treating a viral liver infection in a subject.

Some embodiments also include the use of any one of the compounds provided herein in combination with an additional therapeutic agent.

In some embodiments, the additional therapeutic agent is selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α.

In some embodiments, the additional therapeutic agent comprises interferon-α or pegylated interferon-α.

In some embodiments, the additional therapeutic agent comprises a direct-acting antiviral agent or host targeting antiviral agent. In some embodiments, the direct-acting antiviral agent is selected from the group consisting of an inhibitor of HCV protease, an inhibitor of HCV NS5A replication complex, a nucleoside-based inhibitor of HCV NS5B polymerase, a non-nucleoside inhibitor of HCV NS5B polymerase, and an inhibitor of HCV helicase.

In some embodiments, the viral infection comprises hepatitis C.

In some embodiments, the subject is a mammal.
In some embodiments, the subject is a human.

Some embodiments of the compounds, compositions, and methods provided herein include any one of the compositions provided herein for use in the preparation of a medicament for treating a viral liver infection.

Some embodiments include any one of the compositions provided herein in combination with an additional therapeutic agent.

In some embodiments, the additional therapeutic agent is selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α.

In some embodiments, the additional therapeutic agent comprises interferon-α or pegylated interferon-α.

In some embodiments, the additional therapeutic agent comprises a direct-acting antiviral agent. In some embodiments, the direct-acting antiviral agent is selected from the group consisting of an inhibitor of HCV protease, an inhibitor of HCV NS5A replication complex, a nucleoside-based inhibitor of HCV NS5B polymerase, a non-nucleoside inhibitor of HCV NS5B polymerase, and an inhibitor of HCV helicase.

In some embodiments, the viral infection comprises hepatitis C (HCV).

In some embodiments, the subject is a mammal.
In some embodiments, the subject is a human.

DETAILED DESCRIPTION

The present invention relates to compounds of Formula I, stereoisomers, pharmaceutically acceptable salts or prodrugs thereof or pharmaceutically acceptable salts of the prodrugs as represented by Formula I:

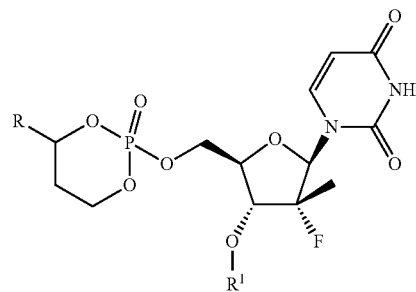

Formula I wherein:

R is an optionally substituted phenyl or an optionally substituted pyridyl;

$R^1$ is selected from the group of a $C_1$-$C_6$ alkyl, a $C_1$-$C_6$ haloalkyl, a $C_1$-$C_6$ heteroalkyl, a $C_1$-$C_6$ acyl, a $C_1$-$C_6$ haloacyl, a $C_1$-$C_6$ heteroacyl, and a $C_1$-$C_6$ haloheteroacyl; provided that $R^1$ is not propionyl;

or a pharmaceutically acceptable salt thereof.

In some embodiment, R is selected from the group consisting of:

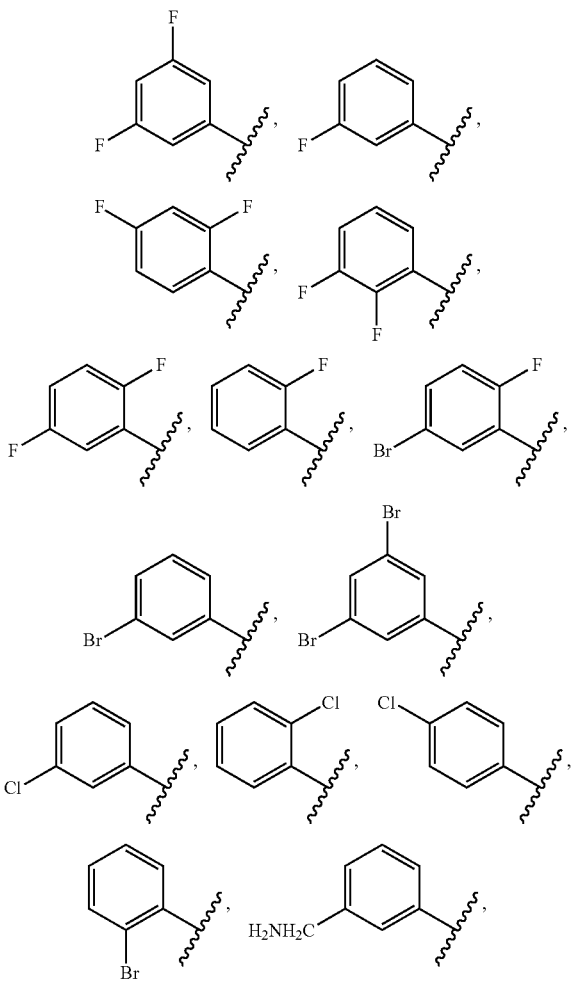

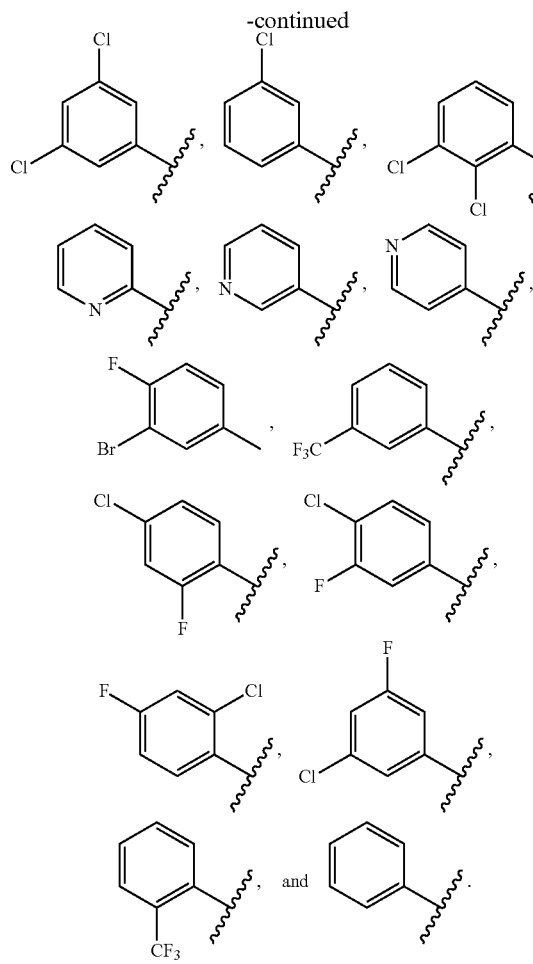

In some embodiments, R is selected from the group consisting of:

In some embodiments, $R^1$ is selected from the group of a $C_1$-$C_6$ alkyl, a $C_1$-$C_6$ heteroalkyl.

In some embodiments, $R^1$ is a $C_1$-$C_6$ acyl; provided that $R^1$ is not propionyl.

In some embodiments, $R^1$ is selected from the group of a $C_1$-$C_6$ haloacyl, a $C_1$-$C_6$ heteroacyl, and a $C_1$-$C_6$ haloheteroacyl.

In some embodiments, $R^1$ is selected from the group consisting of —C(=O)C(NH$_2$)R$^2$, —CH$_2$R$^3$, —C(=O)CH$_3$, —C(=O)CF$_3$, —C(=O)CH$_2$CF$_3$, —C(=O)CH$_2$OCH$_3$, and —C(=O)OCH$_2$CH$_3$, wherein $R^2$ is alkyl; $R^3$ is selected from —OH, —CH$_3$, or —O—C(=O)CH$_3$.

In some embodiments, Formula I is selected from the group consisting of

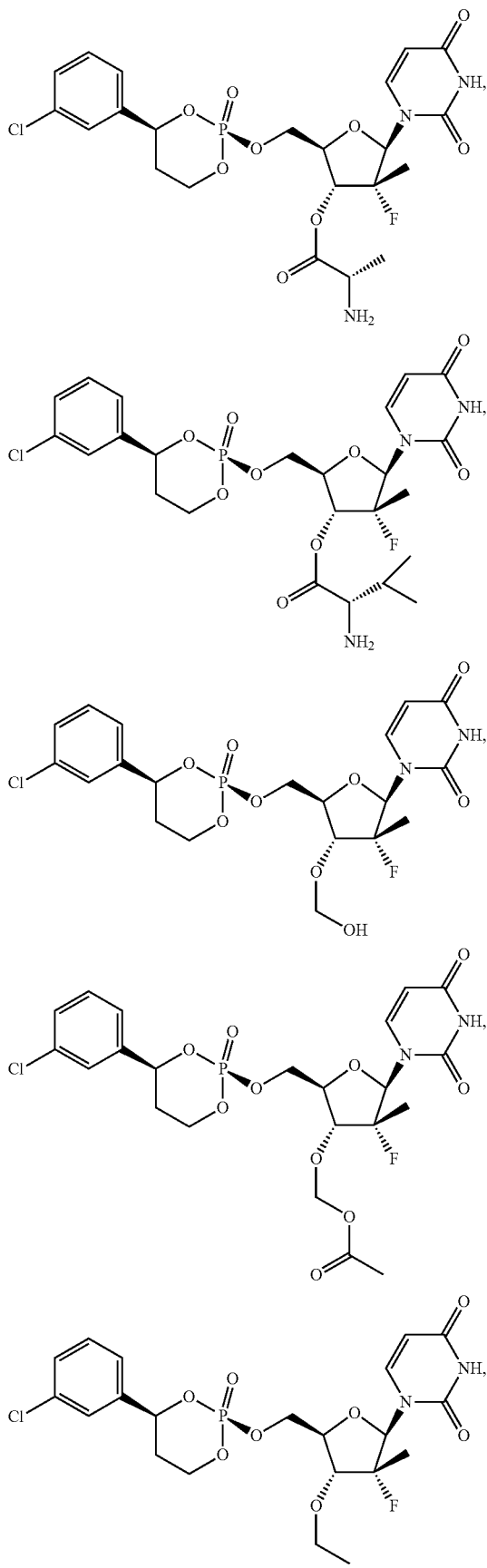

-continued

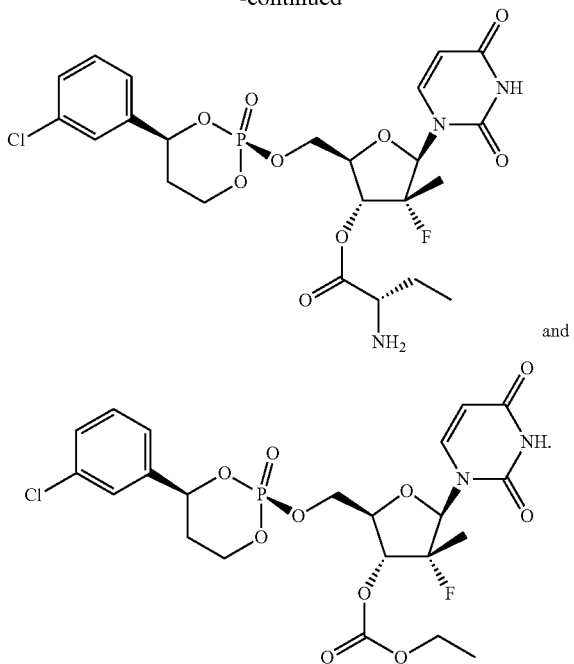

and

Compounds of Formula I have asymmetric centers where the stereochemistry is unspecified, and the diastereomeric mixtures of these compounds are included, as well as the individual stereoisomers when referring to a compound of Formula I generally.

Some embodiments of the compounds, compositions and methods provided herein include a pharmaceutical composition comprising a compound provided herein and a pharmaceutically acceptable carrier.

Some embodiments of the compounds, compositions and methods provided herein include a method of treating a viral liver infection comprising administering an effective amount of a compound provided herein to a subject in need thereof.

Some embodiments also include administering an effective amount of a second or multiple therapeutic agents in combination with a compound provided herein to the subject in need thereof In some embodiments, the second or multiple therapeutic agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α.

In some embodiments, the second therapeutic agent is interferon-α or pegylated interferon-α, alone or in combination with other antiviral agents.

In some embodiments, the multiple therapeutic agents are other direct acting antivirals.

In some embodiments, the direct acting antivirals are selected from the group consisting of an inhibitor of HCV protease, an inhibitor of HCV NS5A replication complex, a nucleoside-based inhibitor of HCV NS5B polymerase, a non-nucleoside inhibitor of HCV NS5B polymerase, and an inhibitor of HCV helicase.

In some embodiments, the viral infection is an infection of the liver.

In some embodiments, the viral infection is HCV.

In some embodiments, the subject is mammalian.

In some embodiments, the subject is human.

Some embodiments of the compounds, compositions and methods provided herein include a method of inhibiting viral replication in a cell comprising contacting the cell with the compound of the claims.

In some embodiments, the viral replication is RNA-dependent.

In some embodiments, the viral replication is HCV replication.

Some embodiments also include contacting the cell with a second or multiple antiviral agents.

In some embodiments, second or multiple antiviral agents are selected from the group consisting of thymosin alpha-1, interferon-λ, an inhibitor of HCV protease, an inhibitor of HCV NS5A replication complex, an inhibitor of HCV NS5B polymerase, a cyclophilin inhibitor, an inhibitor of inosine monophosphate dehydrogenase, ribavirin, interferon-α, and pegylated interferon-α.

In some embodiments, the second antiviral agent is interferon-α or pegylated interferon-α, alone or in combination with other antiviral agents.

In some embodiments, the cell is in vivo.

In some embodiments, the cell is ex vivo.

In some embodiments, the cell is a hepatocyte.

In some embodiments, the cell is mammalian.

In some embodiments, the cell is human.

Some embodiments of the compounds, compositions and methods provided herein include use of a compound provided herein in the treatment of a viral infection.

Some embodiments include the use of a compound provided herein in combination with a second therapeutic agent for the treatment of a viral infection.

In some embodiments, the second or multiple therapeutic agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α.

In some embodiments, the second therapeutic agent is interferon-α or pegylated interferon-α, alone or in combination with other direct acting antivirals.

In some embodiments, the second therapeutic agent is a direct acting antiviral agent.

In some embodiments, the direct acting antiviral agent is selected from the group consisting of an inhibitor of HCV protease, an inhibitor of HCV NS5A replication complex, an inhibitor of HCV NS5B polymerase, and an inhibitor of HCV helicase.

In some embodiments, the viral infection is an infection of the liver.

In some embodiments, the viral infection is HCV.

In some embodiments, the subject is mammalian.

In some embodiments, the subject is human.

Definitions

In accordance with the present invention and as used herein, the following terms are defined with the following meanings, unless explicitly stated otherwise.

The term "alkyl" refers to saturated aliphatic groups including straight-chain, branched chain and cyclic groups, up to and including 10 carbon atoms. Suitable alkyl groups include methyl, ethyl, n-propyl, isopropyl, and cyclopropyl. The alkyl may be optionally substituted with 1-3 substituents.

The term "optionally substituted" or "substituted" includes groups substituted by one to four substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower carboxamidoalkylaryl, lower carboxamidoaryl, lower hydroxyalkyl, lower haloalkyl, lower alkylaminoalkylcarboxy, lower aminocarboxamidoalkyl, cyano, lower alkoxyalkyl, lower perhaloalkyl, and lower arylalkyloxyalkyl. "Substituted aryl" and "substituted heteroaryl" refers to aryl and heteroaryl groups substituted with 1 6 substituents. These substituents are selected from the group consisting of lower alkyl, lower alkoxy, lower perhaloalkyl, halogen, hydroxy, cyano, and amino.

The term "heteroalkyl" refer to alkyl groups containing at least one heteroatom, in a further aspect are 1 to 3 heteroatoms. Suitable heteroatoms include oxygen, sulfur, and nitrogen.

The term "heteroacyl" refer to —C(O)-heteroalkyl groups.

The term "acyloxy" refers to OC(O)R where R is alkyl, or heteroalkyl.

The term "alkoxy" or "alkyloxy" refers to OR where R is alkyl, or heteroalkyl, all optionally substituted.

The term "carboxyl" refers to C(O)OH.

The term "oxo" refers to =O in an alkyl or heterocycloalkyl group.

The term "amino" refers to NRR' where R and R' are independently selected from hydrogen, alkyl, aryl, aralkyl and heterocycloalkyl, all except H are optionally substituted; and R and R' can form a cyclic ring system.

The term "halogen" or "halo" refers to F, Cl, Br and I.

The term "haloalkyl" refer to alkyl groups containing at least one halogen, in a further aspect are 1 to 3 haloatoms. Suitable haloatoms include F, Cl, and Br.

The term "haloheteroalkyl" refer to alkyl groups containing at least one halogen and one heteroatom.

The term "haloacyl" refer to —C(O)-haloalkyl groups.

The term "haloheteroacyl" refer to —C(O)-haloheteroalkyl groups. [0099]

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl. "1 Alkenyl" refers to alkenyl groups where the double bond is between the first and second carbon atom. If the 1 alkenyl group is attached to another group, e.g. it is a W substituent attached to the cyclic phosphate, it is attached at the first carbon.

The term "alkynyl" refers to unsaturated groups which have 2 to 12 atoms and contain at least one carbon carbon triple bond and includes straight chain, branched chain and cyclic groups. Alkynyl groups may be optionally substituted. Suitable alkynyl groups include ethynyl. "1 Alkynyl" refers to alkynyl groups where the triple bond is between the first and second carbon atom. If the 1 alkynyl group is attached to another group, e.g. it is a W substituent attached to the cyclic phosphate, it is attached at the first carbon.

The term "alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched or cyclic. The alkylene may be optionally substituted with 1-3 substituents.

The term "aminoalkyl" refers to the group NR2 alk wherein "alk" is an alkylene group and R is selected from H, alkyl, aryl, aralkyl, and heterocycloalkyl.

The term "alkylaminoalkyl" refers to the group alkyl NR alk wherein each "alk" is an independently selected alkylene, and R is H or lower alkyl. "Lower alkylaminoalkyl" refers to groups where the alkyl and the alkylene group is lower alkyl and alkylene, respectively.

The term "alkoxyalkyl" or "alkyloxyalkyl" refer to the group alkyl 0 alk wherein "alk" is an alkylene group. In "lower alkoxyalkyl", each alkyl and alkylene is lower alkyl and alkylene, respectively.

The terms "alkylthio" refers to the group alkyl S.

The term "alkylthioalkyl" refers to the group alkyl S alk wherein "alk" is an alkylene group. In "lower alkylthioalkyl" each alkyl and alkylene is lower alkyl and alkylene, respectively.

The term "amido" refers to the NR2 group next to an acyl or sulfonyl group as in NR2 C(O), RC(O) NR1, NR2 S(=O)2 and RS(=O)2 NR1, where R and R1 include H, alkyl, aryl, aralkyl, and heterocycloalkyl.

The term "carboxamido" refer to NR2 C(O) and RC(O) NR1, where R and R1 include H, alkyl, aryl, aralkyl, and heterocycloalkyl. The term does not include urea, NR C(O) NR.

The term "acylalkyl" refers to an alkyl C(O) alk, where "alk" is alkylene.

The term "perhalo" refers to groups wherein every C H bond has been replaced with a C halo bond on an aliphatic or aryl group. Suitable perhaloalkyl groups include CF3 and CFCl2.

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+) 7,7 dimethyl 2 oxobicyclo[2.2.1]heptane 1 methanesulfonic acid, citric acid, 1,2 ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2 hydroxyethanesulfonic acid, lactic acid, lactobionic acid, maleic acid, methanesulfonic acid, methylbromide acid, methyl sulfuric acid, 2 naphthalenesulfonic acid, nitric acid, oleic acid, 4,4' methylenebis [3 hydroxy 2 naphthalenecarboxylic acid], phosphoric acid, polygalacturonic acid, stearic acid, succinic acid, sulfuric acid, sulfosalicylic acid, tannic acid, tartaric acid, terphthalic acid, and p toluenesulfonic acid.

The term "naturally-occurring L-amino acid" refers to those amino acids routinely found as components of proteinaceous molecules in nature, including alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine and histidine. In one aspect, this term is intended to encompass L-amino acids having only the amine and carboxylic acid as charged functional groups, i.e., alanine, valine, leucine, isoleucine, proline, phenylalanine, tryptophan, methionine, glycine, serine, threonine, cysteine and tyrosine. In another aspect they are alanine, valine, leucine, isoleucine, proline, phenylalanine, and glycine. In a further aspect, it is valine.

The term "patient" refers to an animal being treated including a mammal, such as a dog, a cat, a cow, a horse, a sheep, and a human. Another aspect includes a mammal, both male and female.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO, HS, HOOC, R2N, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352 401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980, all of which are incorporated by reference in their entireties.

The term "cyclic phosphate ester of 1,3-propanediol", "cyclic phosphate diester of 1,3-propanediol", "2 oxo $2\lambda^5$ [1,3,2]dioxaphosphorinane", "2-oxo-[1,3,2]-dioxaphosphorinane", or "dioxaphosphorinane" refers to the following:

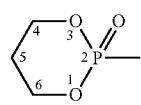

The term "cis" stereochemistry refers to the spatial relationship of the R group and the substituent attached to the phosphorus atom via an exocyclic single bond on the six membered 2-oxo-phosphorinane ring. The structures A and B below show two possible cis-isomers of 2- and 4-substituted 2-oxo-phosphorinane. Structure A shows cis-isomer of (2S,4R)-configuration whereas structure B shows cis-isomer of (2R,4S)-configuration.

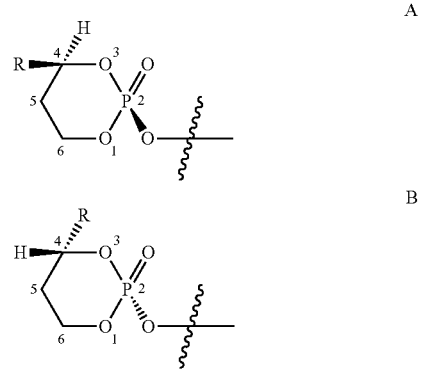

The term "trans" stereochemistry refers to the spatial relationship of the R group and the substituent attached to the phosphorus atom via an exocyclic single bond on the six membered 2-oxo-phosphorinane ring. The structures C and D below show two possible trans-isomers of 2- and 4-substituted 2-oxo-phosphorinane. Structure C shows trans-isomer of (2S,4S)-configuration whereas structure D shows trans-isomer of (2R,4R)-configuration.

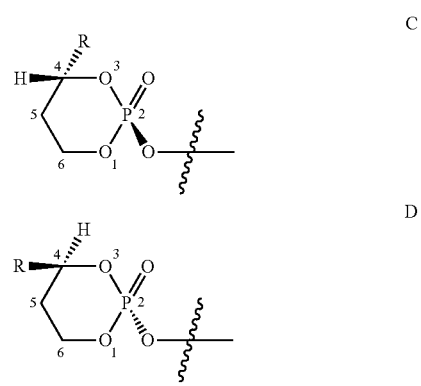

The term "percent enantiomeric excess (% ee)" refers to optical purity. It is obtained by using the following formula:

$$\frac{[R]-[S]}{[R]+[S]} \times 100 = \% R - \% S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

The term "liver" refers to liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

The term "increased or enhanced liver specificity" refers to an increase in the liver specificity ratio in animals treated with the prodrug relative to animals treated with the parent drug. Several phosphoramidate pronucleotide prodrugs, such as GS7977, IDX184, and BMS-986094 (INX-189), showed antiviral activity in clinical studies much better than that of the first generation prodrugs, which raised the hope of developing revolutionary interferon-free antiviral therapies. In addition to the advantage of bypassing the slow first phosphorylation of nucleosides, such prodrugs also generate higher liver nucleotide exposure than in circulation due to high percentage liver first-pass metabolism, which is beneficial in terms of reducing side-effects. The "liver-targeting" effect, however, is not useful as a model because one key enzyme to activate phosphoramide prodrugs, nucleoside phosphoramidase (hint-1), is widely distributed beyond the liver. Any of the prodrugs or phosphoramide-containing metabolites surviving the liver first-pass may end up in other tissues including, for example, the heart. This may explain the cardiovascular toxicity observed by BMS-986094 in clinical trials. Compounds disclosed in U.S. Pat. Nos. 8,063,025, 7,666,855, and PCT Pub. No. WO2009/073506, are designed for the liver-specific delivery of nucleosides for the treatment of HCV patients and take advantage of a cytochrome P450 enzyme that is mainly expressed in the liver.

The term "enhanced oral bioavailability" refers to an increase of at least 50% of the absorption of the dose of the parent drug. In an additional aspect the increase in oral bioavailability of the prodrug (compared to the parent drug) is at least 100%, that is a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biological activity of the drug and the ability of an agent to bypass this resistance through the use of alternative pathways or the failure of the agent to induce changes that tend to resistance.

The terms "treating" or "treatment" of a disease includes inhibiting the disease (slowing or arresting its development), providing relief from the symptoms or side effects of the disease (including palliative treatment), and relieving the disease (causing regression of the disease).

Formulations

Compounds of the invention are administered in a total daily dose of 0.01 to 1000 mg/kg. In one aspect the range is about 0.1 mg/kg to about 100 mg/kg. In another aspect the range is 0.5 to 20 mg/kg. The dose may be administered in as many divided doses as is convenient.

Compounds of this invention when used in combination with other antiviral agents may be administered as a daily dose or an appropriate fraction of the daily dose (e.g., bid). Administration of the prodrug may occur at or near the time in which the other antiviral is administered or at a different time. The compounds of this invention may be used in a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

Pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachid oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachid oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The amount of active ingredient that may be combined with the carrier material to produce a single dosage form will vary depending upon the host treated and the particular mode of administration. For example, a time-release formulation intended for oral administration to humans may contain 20 to 2000 µmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 µmol (approximately 0.025 to 25 mg) of the active ingredient per milliliter of solution in order that infusion of a suitable volume at a rate of about 30 mL/h can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for parenteral administration may be administered in a continuous infusion manner via an indwelling pump or via a hospital bag. Continuous infusion includes the infusion by an external pump. The infusions may be done through a Hickman or PICC or any other suitable means of administering a formulation either parenterally or i.v.

Preferred unit dosage formulations are those containing a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Some embodiments are concerned with a method of inhibiting HCV replication or treating HCV infection with a compound provided herein in combination with one or more agents useful for treating HCV infection. Such agents active against HCV include, but are not limited to, ribavirin, thymosin alpha-1, interferon-β, interferon-α, interferon-λ, pegylated interferon-α(peginterferon-α), Interferon-α includes, but is not limited to, recombinant interferon-α2a (such as Roferon interferon available from Hoffmann-La-Roche, Nutley, N.J.), pegylated interferon-α2a (Pegasys™), interferon-α2b (such as Intron-A interferon available from Merck), pegylated interferon-α2b (PegIntron™), a recombinant consensus interferon (such as interferon alphacon-1), and a purified interferon-α product. Amgen's recombinant consensus interferon has the brand name Infergen®. Some embodiments are therefore to be understood as embracing all such regimes of simultaneous or alternating treatment, and the term "administering" is to be interpreted accordingly. It will be understood that the scope of combinations of the compounds provided herein with other agents useful for treating HCV infection includes in principle any combination with any pharmaceutical composition for treating HCV infection. When a compound provided herein or a pharmaceutically acceptable salt thereof is used in combination with a second therapeutic agent active against HCV, the dose of each compound may be either the same as or different from the dose when the compound is used alone.

Some embodiments include a pharmaceutical composition comprising a compound of Formula I or pharmaceutically acceptable salt thereof and at least one agent useful for treating a viral infection, particularly an HCV infection.

For the treatment of HCV infection, the compounds provided herein may also be administered in combination with an agent that is an inhibitor of HCV protease. HCV protease is an essential viral enzyme and has been demonstrated to be an excellent target for inhibition of HCV replication. Specific embodiments of HCV protease inhibitors for combination with the compounds provided herein are telaprevir, boceprevir, faldaprevir, simeprevir, vaniprevir, asunaprevir, danoprevir, ACH-1625, ACH-2684, ABT-450, GS-9256, GS-9451, MK-5172, and IDX320.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds provided herein may also be administered in combination with an inhibitor of IMPDH, such as VX-497 (merimepodib), which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, Agents Action, 44 (Suppl.): 165 (1993)].

The compounds provided herein may also be combined for the treatment of HCV infection with nucleoside-based inhibitors of HCV NS5B polymerase. Such inhibitors include, but are not limited to, GS-7977, mericitabine, GS-6620, IDX184, IDX368, ALS-2200, BCX5191, and EP-NI266.

The compounds provided herein may also be combined for the treatment of HCV infection with non-nucleoside inhibitors of HCV polymerase. Such inhibitors include, but are not limited to, setrobuvir, ABT-333, ABT-072, BI207127, filibuvir, BMS-791325, tegobuvir, VX-222, GS-9669, TMC647055, PPI-383, and VLS-732.

The compounds provided herein may also be combined for the treatment of HCV infection with inhibitors of HCV NS5A replication complex. Such inhibitors include, but are not limited to, daclatasvir, GS-5885, ABT-267, R05466731, GSK2336805, IDX719, ACH-2928, ACH-3102, JNJ-47910382, MK-8742, PPI-668, PPI-461, and BMS-824393.

The compounds provided herein may also be combined for the treatment of HCV infection with cyclophilin inhibitors. Such inhibitors include, but are not limited to, alisporivir, NIM811, and BC556.

The compounds provided herein may also be combined for the treatment of HCV infection with other types of inhibitors. Such inhibitors include, but are not limited to, BMS-914143, miravirsen, BMS-929075, MK-6325, MK-2748, MK-8325, ITX 5061, BL-8020, infradure, and TG4040.

Synthesis of Compounds of 2'-C-methyl Derivatives

Synthesis of the 5'-nucleoside monophosphate (NMP) prodrugs of the present invention is organized into two sections: 1) synthesis of phosphorylation precursors; 2) synthesis of prodrugs via coupling of nucleosides and prodrug moiety. General synthesis of the compounds of liver-targeting nucleoside prodrug derivatives has been discussed in detail previously (U.S. Pat. No. 7,666,855).

Scheme I describes general strategies of synthesis of the 2'-methyl nucleoside analogs. The first strategy starts with protection of the 3'-hydroxy group of nucleosides of structure 1 to generate intermediates of structure 2. The phosphate group is introduced by reaction of compounds of structure 2 and a reagent of structure 3 to give the monophosphate compounds of structure 4 following a deprotection of the 3'-hydroxy group. Treatment of compounds of structure 4 with a reagent of structure 5 provides the final compounds of structure 6. Alternatively, nucleoside of structure 1 can be phosphorylated directly with reagent of structure 3 without protection of the 3'-hydroxy group and then be acylated to afford the final compounds of structure 6. The third strategy is to prepare the intermediates of structure 7 and then is converted to final compounds of structure 6 by treatment with reagent of structure 3.

Scheme I
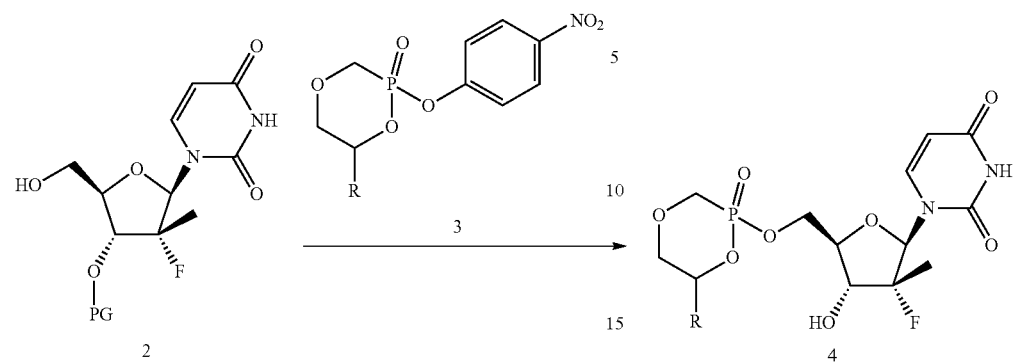
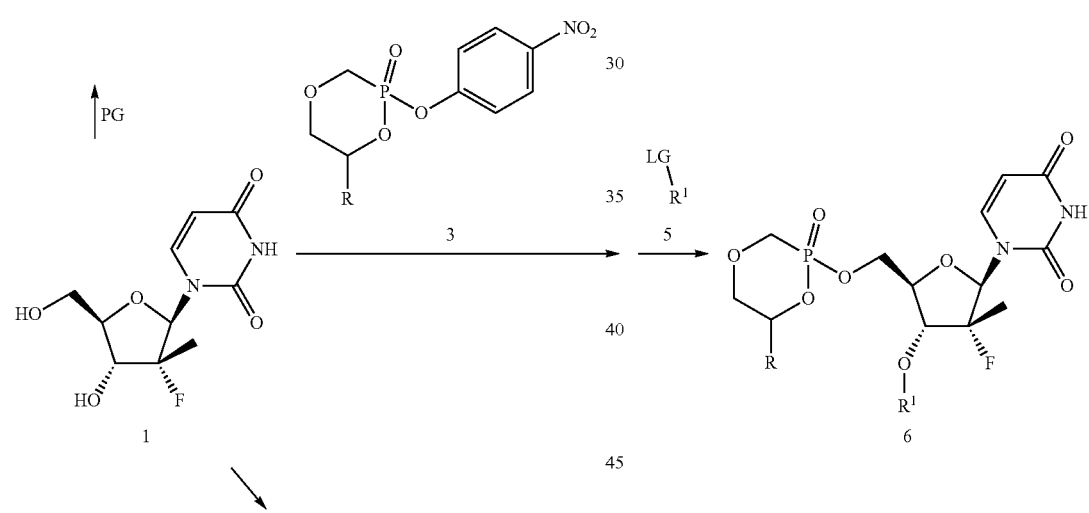
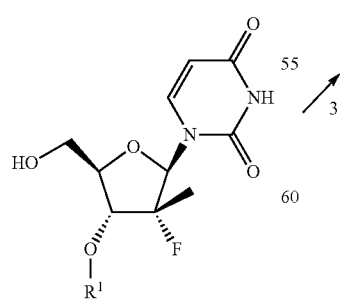

EXAMPLES

Some compounds of Formula I are prepared as outlined below.

Example 1

2(R)-Uracilyl-5(R)-(4(S)-(3-chlorophenyl)-2-oxo-1,3,2-dioxaphosphorinan-2(R)-yloxymethyl)-3(R)-fluoro-4(R)-(1-oxo-2(S)-aminopropyloxy)-3(R)-methyltetrahydrofuran (Compound 101)

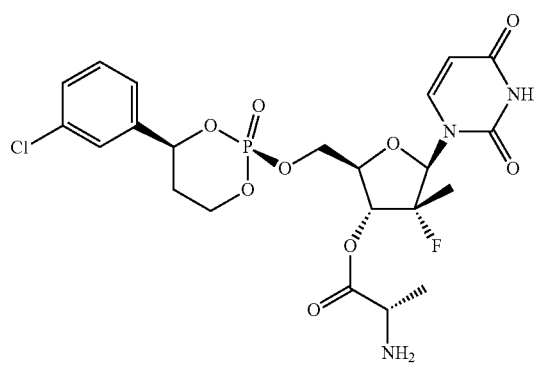

Compound 101 was prepared according to synthetic strategy of Scheme I from 2'-deoxy-2'-fluoro-2'-β-C-methyluridine. $MH^+$=562.1.

Example 2

2(R)-Uracilyl-5(R)-(4(S)-(3-chlorophenyl)-2-oxo-1,3,2-dioxaphosphorinan-2(R)-yloxymethyl)-3(R)-fluoro-4(R)-(1-oxo-2(S)-amino-3-methylbutyloxy)-3(R)-methyltetrahydrofuran (Compound 102)

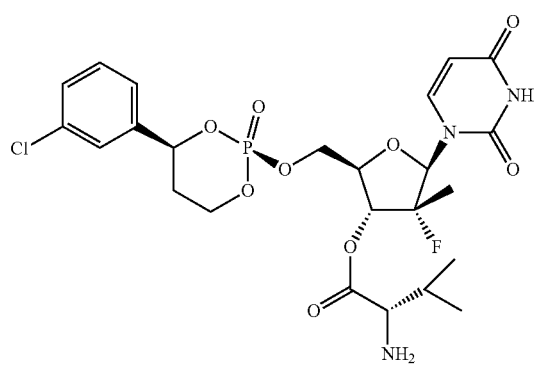 [SMILES: CC(C)[C@H](N)C(=O)O[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 102 was prepared according to synthetic strategy of Scheme I from 2'-deoxy-2'-fluoro-2'-β-C-methyluridine. $MH^+$=590.2.

Example 3

2(R)-Uracilyl-5(R)-(4(S)-(3-chlorophenyl)-2-oxo-1,3,2-dioxaphosphorinan-2(R)-yloxymethyl)-3(R)-fluoro-4(R)-hydroxymethoxy-3(R)-methyltetrahydrofuran (Compound 103)

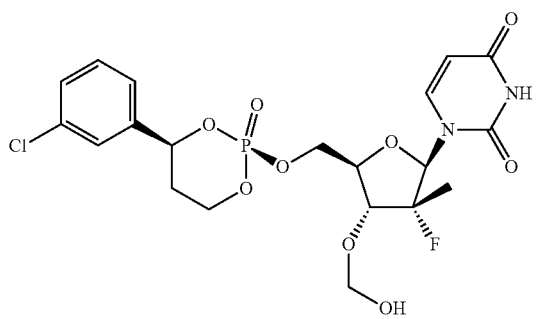 [SMILES: C[C@@]1(F)[C@H](OCO)[C@@H](CO[P@@]2(=O)OCC[C@@H](c3cccc(Cl)c3)O2)O[C@H]1n1ccc(=O)[nH]c1=O]

Compound 103 can be prepared according to synthetic strategy of Scheme I from 2'-deoxy-2'-fluoro-2'-β-C-methyluridine.

Example 4

2(R)-Uracilyl-5(R)-(4(S)-(3-chlorophenyl)-2-oxo-1,3,2-dioxaphosphorinan-2(R)-yloxymethyl)-3(R)-fluoro-4(R)-acetyloxymethoxy-3(R)-methyltetrahydrofuran (Compound 104)

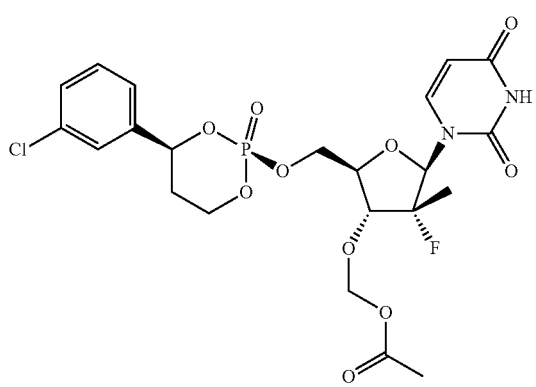 [SMILES: CC(=O)OCO[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 104 can be prepared according to synthetic strategy of Scheme I from 2'-deoxy-2'-fluoro-2'-β-C-methyluridine.

Example 5

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-ethoxy-3(R)-methyltetrahydrofuran
(Compound 105)

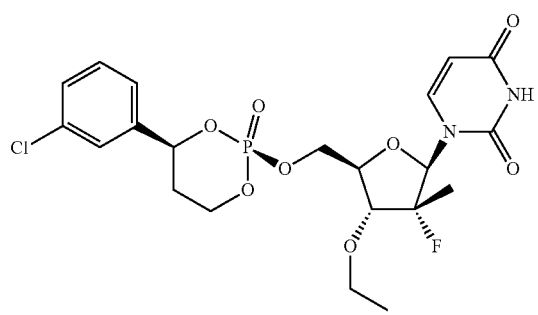 [SMILES: CCO[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 105 can be prepared according to synthetic strategy of Scheme I from 2'-deoxy-2'-fluoro-2'-β-C-methyluridine.

Example 6

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-(1-oxo-2(S)-aminobutyloxy)-3(R)-methyltetrahydrofuran (Compound 106)

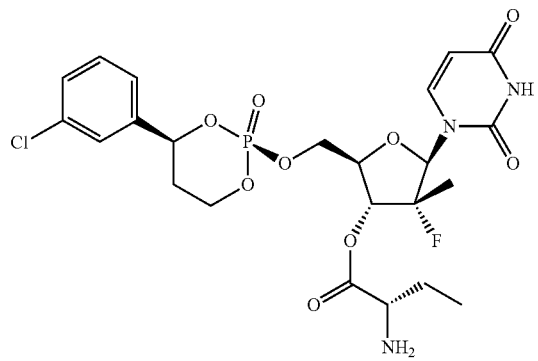

Compound 106 was prepared according to synthetic strategy of Scheme I from 2'-deoxy-2'-fluoro-2'-β-C-methyluridine. MH$^+$=576.2.

Example 7

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-ethoxycarbonyloxy-3(R)-methyltetrahydrofuran (Compound 107)

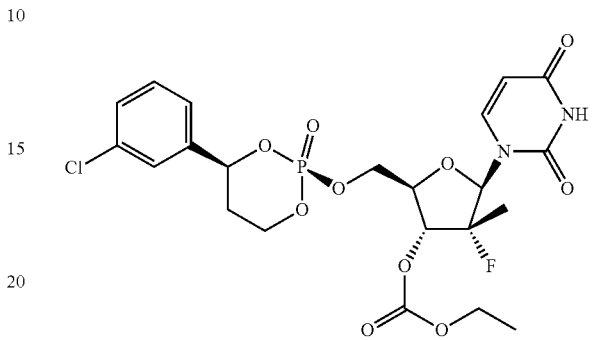

Compound 107 was prepared according to synthetic strategy of Scheme I from 2'-deoxy-2'-fluoro-2'-β-C-methyluridine. MH$^+$=563.1.

Example 8

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-acetyloxy-3(R)-methyltetrahydrofuran
(Compound 108)

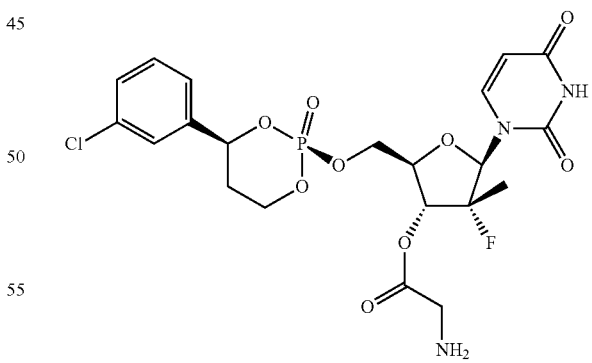

Compound 108 was prepared according to synthetic strategy of Scheme I from 2'-deoxy-2'-fluoro-2'-β-C-methyluridine. MH$^+$=548.1.

Example 9

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-methoxyacetyloxy-3(R)-methyltetrahy-
drofuran (Compound 109)

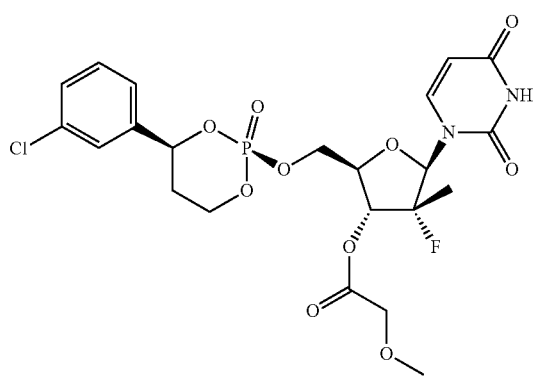 [SMILES: COCC(=O)O[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 109 was prepared according synthetic strategy of Scheme I from 2'-deoxy-2'-fluoro-2'-β-C-methyluridine. MH$^+$=563.1.

Example 10

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-methoxycarbonyloxy-3(R)-methyltetra-
hydrofuran (Compound 110)

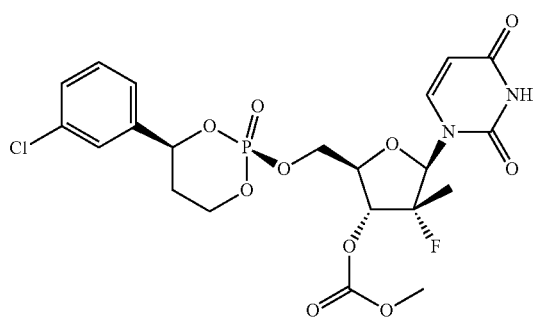 [SMILES: COC(=O)O[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 110 was prepared according to synthetic strategy of Scheme I from 2'-deoxy-2'-fluoro-2'-β-C-methyluridine. MH$^+$=549.1.

Example 11

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-dimethylaminocarbonyloxy-3(R)-meth-
yltetrahydrofuran (Compound 111)

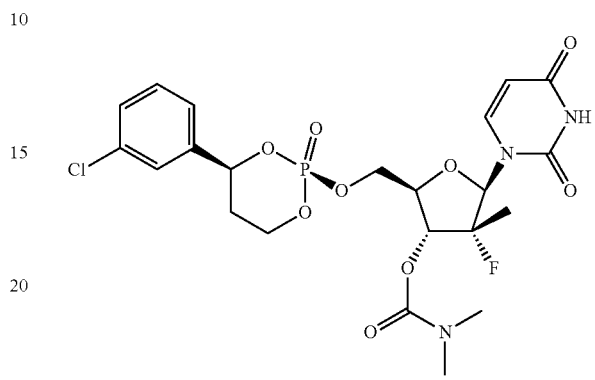

Compound 111 was prepared according to synthetic strategy of Scheme I from 2'-deoxy-2'-fluoro-2'-β-C-methyluridine. MH$^+$=562.1.

Example 12

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-hydroxyacetyloxy-3(R)-methyltetrahy-
drofuran (Compound 112)

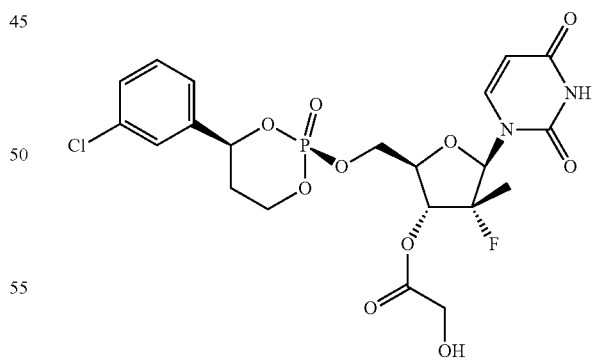

Compound 112 was prepared according to synthetic strategy of Scheme I from 2'-deoxy-2'-fluoro-2'-β-C-methyluridine. MH$^+$=549.1.

Example 13

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-acetyloxy-3(R)-methyltetrahydrofuran
(Compound 113)

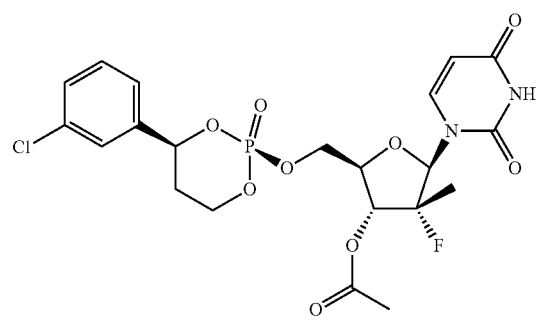

Compound 113 can be prepared according to synthetic strategy of Scheme I from 2'-deoxy-2'-fluoro-2'-β-C-methyluridine.

Example 14

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-(2-methylpropionyloxy)-3(R)-methyltetrahydrofuran (Compound 114)

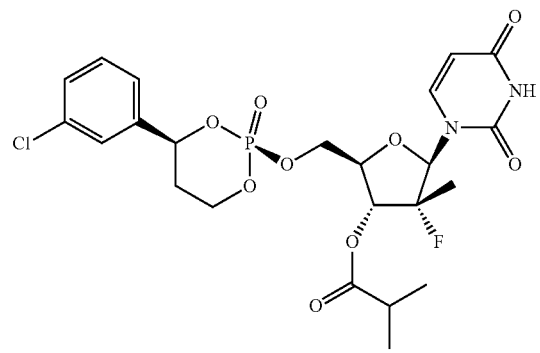 [SMILES: CN(C)C(=O)O[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 114 can be prepared according to synthetic strategy of Scheme I from 2'-deoxy-2'-fluoro-2'-β-C-methyluridine.

Example 15

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-trifluoroacetyloxy-3(R)-methyltetrahydrofuran (Compound 115)

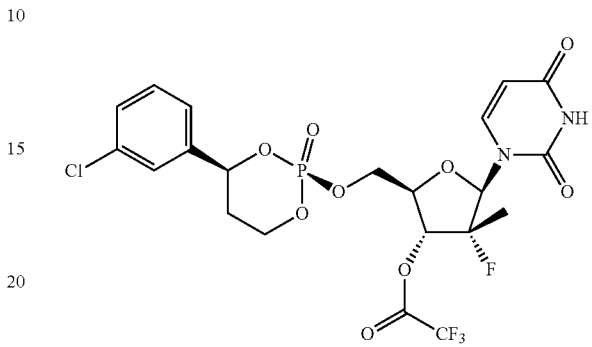

Compound 115 can be prepared according to synthetic strategy of Scheme I from 2'-deoxy-2'-fluoro-2'-β-C-methyluridine.

Example 16

2(R)-Uracilyl-5(R)-(4(S)-(3-chlorophenyl)-2-oxo-1,
3,2-dioxaphosphorinan-2(R)-yloxymethyl)-3(R)-
fluoro-4(R)-trifluoromethoxycarbonyloxy 3(R)-
methyltetrahydrofuran (Compound 116)

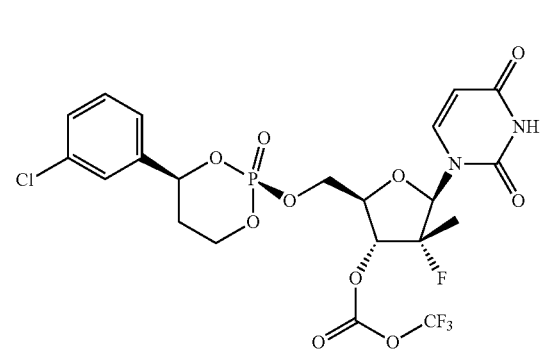 [SMILES: C[C@@]1(F)[C@H](OC(=O)OC(F)(F)F)[C@@H](CO[P@@]2(=O)OCC[C@@H](c3cccc(Cl)c3)O2)O[C@H]1n1ccc(=O)[nH]c1=O]

Compound 116 can be prepared according to synthetic strategy of Scheme I from 2'-deoxy-2'-fluoro-2'-β-C-methyluridine.

Example 17

2(R)-Uracilyl-5(R)-(4(S)-(3-chlorophenyl)-2-oxo-1,3,2-dioxaphosphorinan-2(R)-yloxymethyl)-3(R)-fluoro-4(R)-trifluoromethoxyacetyloxy-3(R)-methyltetrahydrofuran (Compound 117)

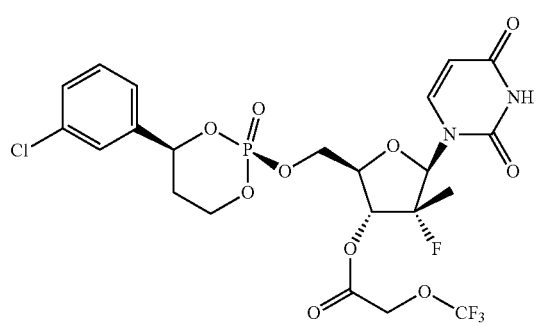 [SMILES: C[C@@]1(F)[C@H](OC(=O)COC(F)(F)F)[C@@H](CO[P@@]2(=O)OCC[C@@H](c3cccc(Cl)c3)O2)O[C@H]1n1ccc(=O)[nH]c1=O]

Compound 117 can be prepared according to synthetic strategy of Scheme I from 2'-deoxy-2'-fluoro-2'-β-C-methyluridine.

Example 18

2(R)-Uracilyl-5(R)-(4(S)-(3-chlorophenyl)-2-oxo-1,3,2-dioxaphosphorinan-2(R)-yloxymethyl)-3(R)-fluoro-4(R)-pivalyloxy-3(R)-methyltetrahydrofuran (Compound 118)

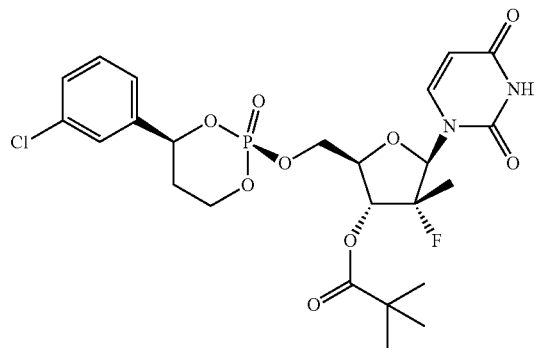 [SMILES: CC(C)(C)C(=O)O[C@@H]1[C@@H](CO[P@@]2(=O)OCC[C@@H](c3cccc(Cl)c3)O2)O[C@@H](n2ccc(=O)[nH]c2=O)[C@]1(C)F]

Compound 118 can be prepared according to synthetic strategy of Scheme I from 2'-deoxy-2'-fluoro-2'-β-C-methyluridine.

Example 19

2(R)-Uracilyl-5(R)-(4(S)-(3-chlorophenyl)-2-oxo-1,3,2-dioxaphosphorinan-2(R)-yloxymethyl)-3(R)-fluoro-4(R)-(3-chloropropionyloxy)-3(R)-methyltetrahydrofuran (Compound 119)

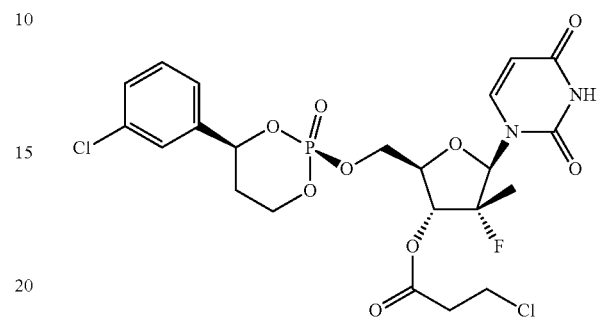

Compound 119 can be prepared according to synthetic strategy of Scheme I from 2'-deoxy-2'-fluoro-2'-β-C-methyluridine.

Example 20

2(R)-Uracilyl-5(R)-(4(S)-(3-chlorophenyl)-2-oxo-1,3,2-dioxaphosphorinan-2(R)-yloxymethyl)-3(R)-fluoro-4(R)-(3,3,3-trifluoropropionyloxy)-3(R)-methyltetrahydrofuran (Compound 120)

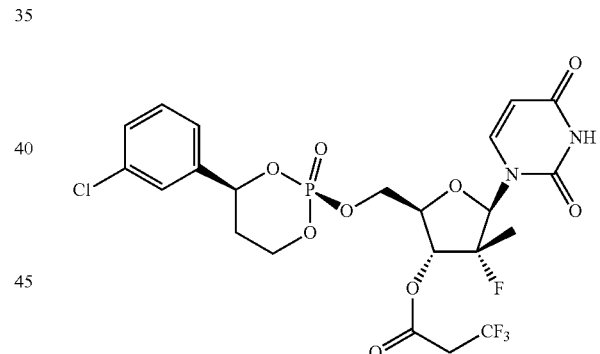

Compound 120 can be prepared according to synthetic strategy of Scheme I from 2'-deoxy-2'-fluoro-2'-β-C-methyluridine.

Biological Examples

Examples of use of the method of the invention include the following. It will be understood that these examples are exemplary and that the method of the invention is not limited solely to these examples. For the purposes of clarity and brevity, chemical compounds are referred to as synthetic example numbers in the biological examples below.

Example A: In Vitro Activation of Prodrug Analogues by Rat Liver Microsomes. Quantification by LC-MS/MS Prodrug analogues were tested for activation to NMP in reactions catalyzed by the microsomal fraction of rat liver.

Methods:

Prodrugs are tested for activation by liver microsomes isolated from rats induced with dexamethasone to enhance CYP3A4 activity ( ) Reactions are conducted in 0.1 M KH2PO4, pH 7.4, in the presence of 2 mM NADPH and liver microsomes (1 mg/mL). Reaction mixtures were incubated for 5 min. in an Eppendorf Thermomixer 5436 (37° C., speed 6). Reactions are terminated by the addition of 1.5 volumes of methanol. The resulting extracts are clarified by centrifugation at 14,000 rpm in an Eppendorf microfuge (20 min.). The supernatants (200 µL) are evaporated under vacuum and heat to dryness. The dried residue is reconstituted with 200 µL of water and the mixture is centrifuged for 10 min at 14,000 rpm. A mixture of 35 µL aliquot of supernatant and 35 µL of mobile phase A (20 mM N—N-dimethylhexylamine and 10 mM propionic acid in 20% methanol) is analyzed by LC-MS/MS (Applied Biosystems, API 4000) equipped with an Agilent 1100 binary pump and a LEAP injector. NMP is detected by using MS/MS mode (M-/78.8) and quantified based on comparison to a standard of lamivudine monophosphate.

Example B: NTP Accumulation in Hepatocytes Following Incubation with Nucleoside Analogues and their Prodrugs Nucleoside analogues and their prodrugs are evaluated for their ability to generate NTPs in freshly isolated rat hepatocytes. It is generally accepted that the NTP form of a nucleoside is the active antiviral agent.

Methods:

Hepatocytes are prepared from fed Sprague-Dawley rats (250-300 g) according to the procedure of Berry and Friend (Berry, M. N. Friend, D. S., J. Cell Biol. 43:506-520 (1969)) as modified by Groen (Groen, A. K. et al., Eur. J. Biochem 122:87-93 (1982)). Hepatocytes (20 mg/mL wet weight, >85% trypan blue viability) are incubated at 37° C. in 2 mL of Krebs-bicarbonate buffer containing 20 mM glucose, and 1 mg/mL BSA for 2 h in the presence of 1-250 µM nucleoside or prodrug (from 25 mM stock solutions in DMSO). Following the incubation, 1600 µL aliquot of the cell suspension is centrifuged and 300 µL of acetonitrile is added to the pellet, vortexed and sonicated until the pellet broke down. Then 200 µL of water is added to make a 60% acetonitrile solution. After 10 min centrifugation at 14,000 rpm, the resulting supernatant is transferred to a new vial and evaporated to near dryness in a Savant SpeedVac Plus at room temperature. The dried residue is reconstituted with 200 µL of water and the mixture is centrifuged for 10 min at 14,000 rpm. A mixture of 35 µL aliquot of supernatant and 35 µL of mobile phase A (20 mM N—N-dimethylhexylamine and 10 mM propionic acid in 20% methanol) is analyzed by LC-MS/MS (Applied Biosystems, API 4000) equipped with an Agilent 1100 binary pump and a LEAP injector. NTP is detected by using MS/MS mode (M-/78.8) and quantified based on comparison to a standard of lamivudine triphosphate.

Example C: Liver NTP and Plasma Nucleoside Levels after Oral Dosing of the Novel Compounds in Male Sprague Dawley Rats Nucleoside prodrugs were evaluated for their ability to generate NTPs in rat liver and the nucleoside in circulation after oral administration. It is generally accepted that the NTP form of a nucleoside is the active antiviral agent. The ratio of liver NTP concentration over plasma nucleoside concentration is used to characterize the liver selectivity generated by the prodrug analogs.

Methods:

HepDirect prodrug analogs of (2'R)-2'-deoxy-2'-fluoro-2'-C-methyluridine were orally administered to Sprague-Dawley rats at nucleoside equivalent doses (20 mg/kg nucleoside). Blood and tissues were harvested and snap-frozen in liquid nitrogen. Plasma nucleoside and tissue NTP concentrations were measured by LC-MS/MS to compare liver-targeting efficiency. Table 1 shows Liver NTP and plasma nucleoside levels 5 hours after oral dosing of the novel and reference compounds in male Sprague Dawley rats.

TABLE 1

| Compound | Liver NTP level (ng/g) | Plasma nucleoside level (ng/mL) | Liver/Plasma |
|---|---|---|---|
| 101 | 10,000 | 220 | 45 |
| 102 | 15,000 | 220 | 68 |
| 106 | 16,900 | 121 | 144 |
| 107 | 25,333 | 168 | 152 |
| 108 | 7,000 | 225 | 31 |
| 109 | 15,267 | 65 | 152 |
| 110 | 49,633 | 366 | 138 |
| 112 | 17,000 | 120 | 145 |
| Sofosbuvir | 6,874 | 211 | 32 |

Results:

The results demonstrate the liver targeting of the nucleoside analog prodrugs as similar or greater extend to sofosbuvir at the given time point.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of preparing a compound of Formula I:

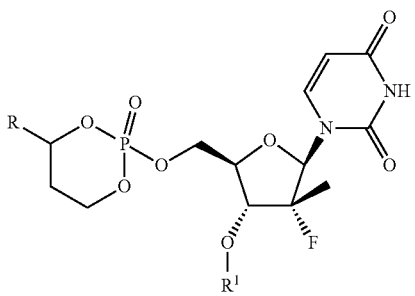

Formula I and pharmaceutically acceptable salts thereof,
wherein:
R is an optionally substituted phenyl or an optionally substituted pyridyl;
$R^1$ is selected from —$CH_2R^{1A}$ and —C(=O)$R^{1B}$;
$R^{1A}$ is selected from hydroxyl, —O—C(=$OCH_3$), and $C_1$-$C_8$ alkyl optionally substituted with one or more $R^{1AA}$;
each $R^{1AA}$ is independently hydroxy, halo, or —O—C(=O)$R^{1AB}$; and
$R^{1AB}$ is $C_1$-$C_8$ alkyl or $C_1$-$C_8$ haloalkyl;
$R^{1B}$ is selected from $C_1$-$C_8$ alkyl optionally substituted with one or more $R^{1BA}$, $C_1$-$C_8$ alkoxy optionally substituted with one or more $R^{1BA}$, and —N($R^{1C}$)$_2$;
each $R^{1C}$ is independently hydrogen or $C_1$-$C_8$ alkyl;
each $R^{1BA}$ is independently hydroxy, halo, —N($R^{1CC}$)$_2$ or —$OR^{1BB}$;
$R^{1BB}$ is $C_1$-$C_8$ alkyl or $C_1$-$C_8$ haloalkyl; and
each $R^{1CC}$ is independently hydrogen or $C_1$-$C_8$ alkyl;
the method comprising:
(a) phosphorylating 2'-deoxy-2'-fluoro-2'-C-methyluridine or a derivative thereof at the 5' hydroxyl group; and
(b) performing nucleophilic substitution at the 3' hydroxyl group of the 2'-deoxy-2'-fluoro-2'-C-methyluridine or derivative thereof.

2. The method of claim 1, protecting the 3' hydroxyl group of the 2'-deoxy-2'-fluoro-2'-C-methyluridine or a derivative thereof prior to step (a).

3. The method of claim 2, deprotecting the phosphorylated 2'-deoxy-2'-fluoro-2'-C-methyluridine derivative prior to step (b).

4. The method of claim 1, wherein step (b) is performed before step (a).

5. The method of claim 1, wherein the phosphorylating comprises reaction with:

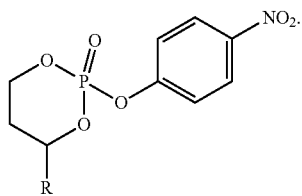

6. The method of claim 1, wherein the nucleophilic substitution comprises reaction with LG-R1, wherein LG is a leaving group.

7. The method of claim 1, wherein R is selected from the group consisting of:

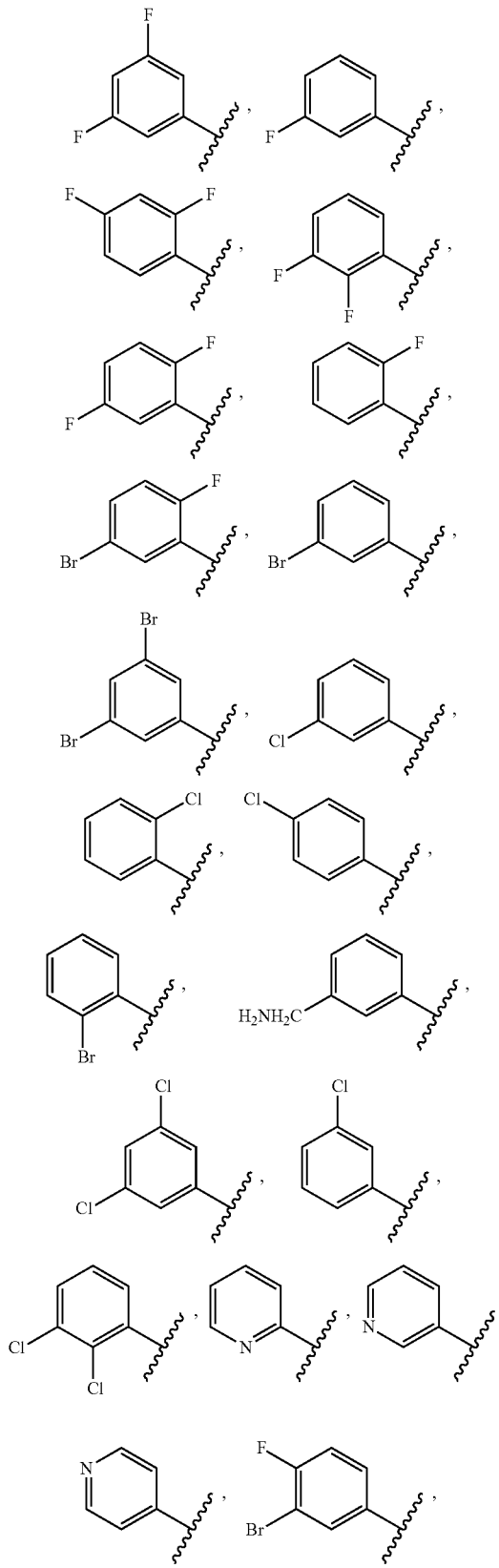

-continued

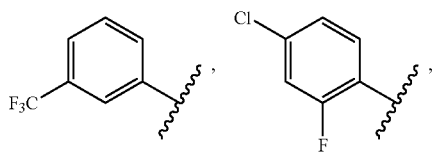

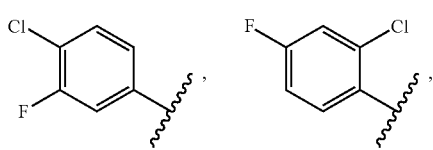

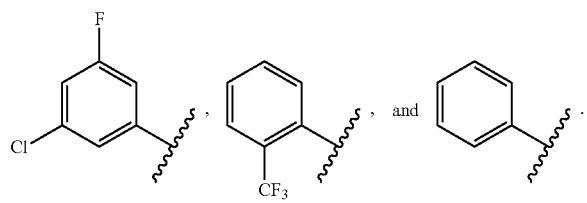

8. The method of claim 1, wherein R is selected from the group consisting of

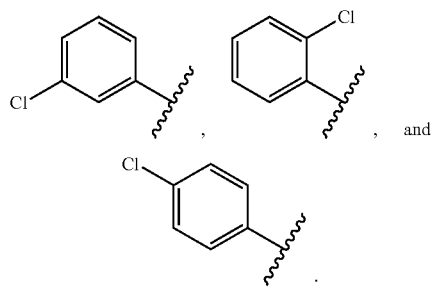

9. The method of claim 1, wherein $R^1$ is —$CH_2R^{1A}$.

10. The method of claim 9, wherein $R^{1A}$ is $C_1$-$C_8$ alkyl substituted with one or more $R^{1AA}$.

11. The method of claim 10, wherein $R^{1AA}$ is hydroxy.

12. The method of claim 10, wherein $R^{1AA}$ is halo.

13. The method of claim 10, wherein $R^{1AA}$ is —O—C(=O)$R^{1AB}$.

14. The method of claim 9, wherein $R^{1A}$ is selected from —OH, —$CH_3$, and —O—C(=O)$CH_3$.

15. The method of claim 1, wherein $R^1$ is —C(=O)$R^{1B}$.

16. The method of claim 15, wherein $R^{1B}$ is $C_1$-$C_8$ alkyl optionally substituted with one or more $R^{1BA}$.

17. The method of claim 15, wherein $R^{1B}$ is $C_1$-$C_8$ alkoxy optionally substituted with one or more $R^{1BA}$.

18. The method of claim 15, wherein $R^{1B}$ is —N($R^{1C}$)$_2$.

19. The method of claim 15, wherein $R^{1B}$ is selected from —C(NH$_2$)$C_{1-6}$alkyl and —OCH$_2$CH$_3$.

20. The method of claim 1, wherein the compound is selected from the group consisting of:

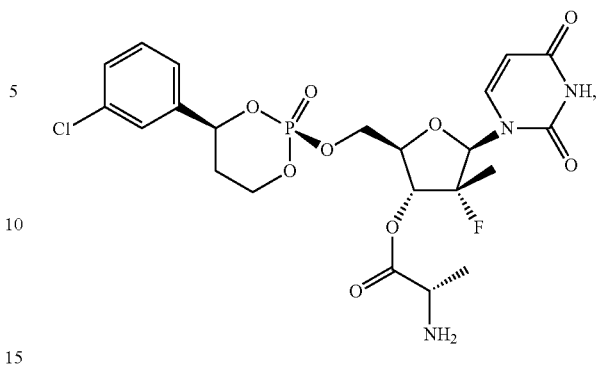

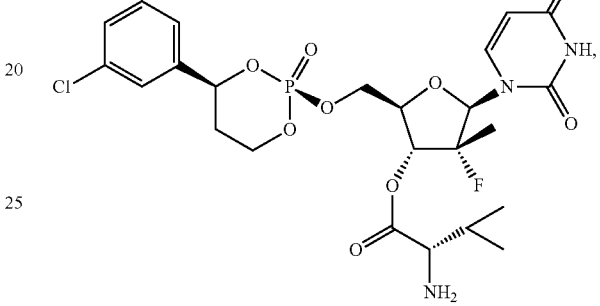

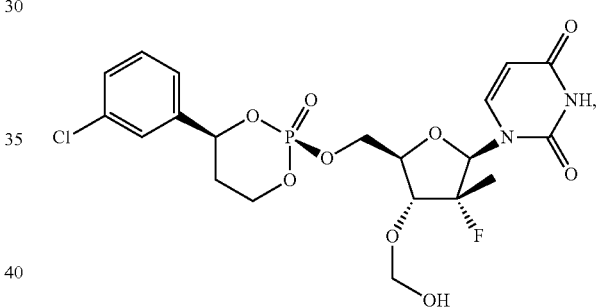

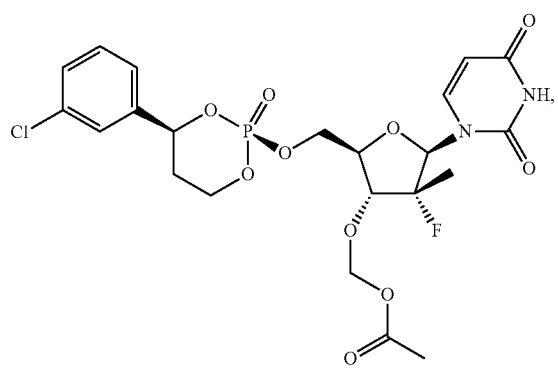

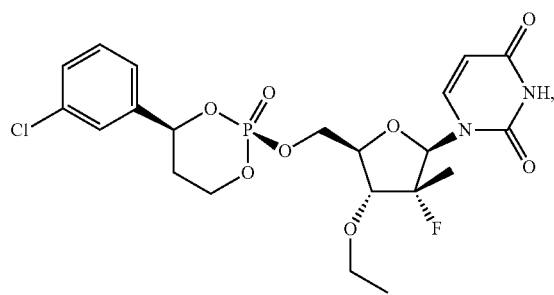

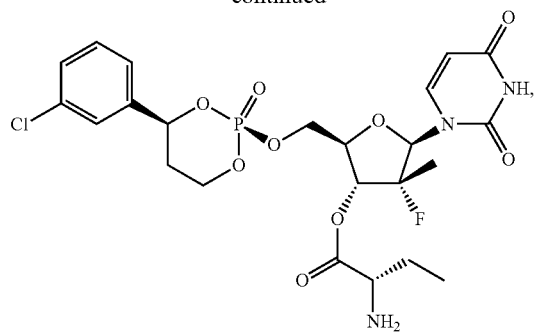
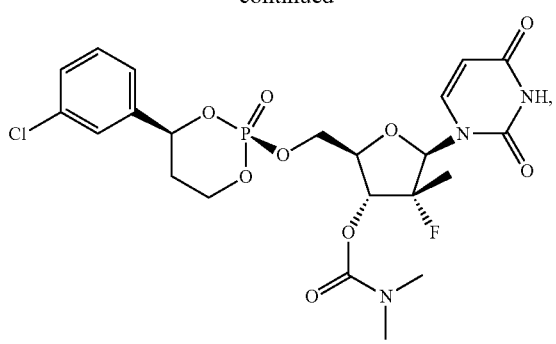
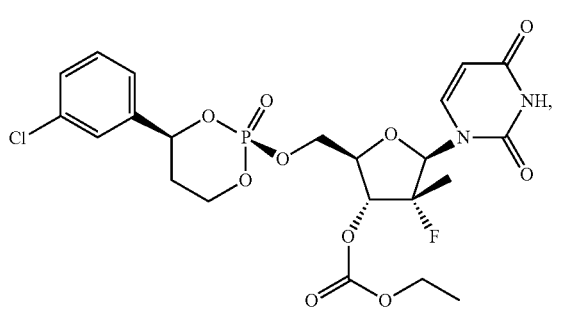
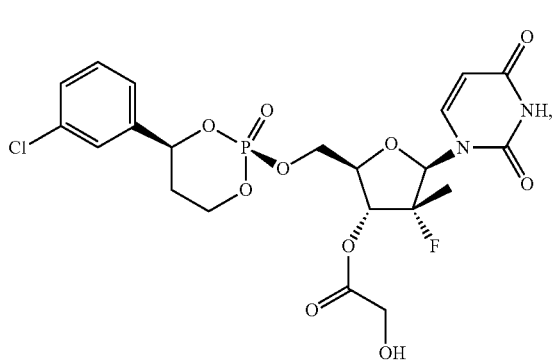
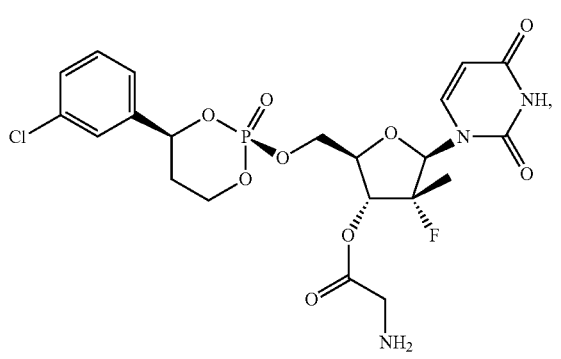
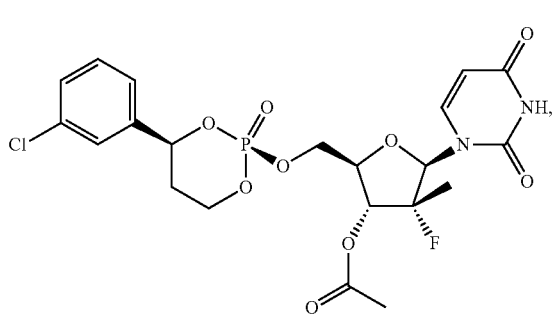
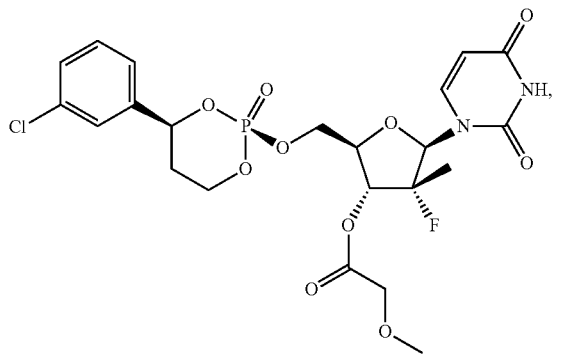
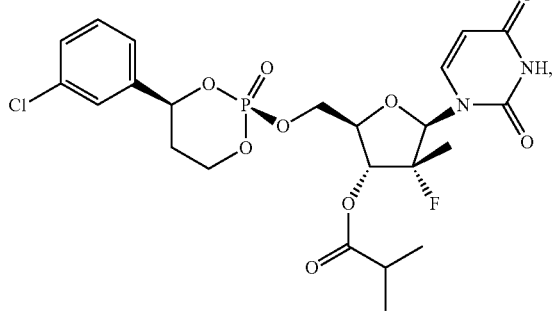
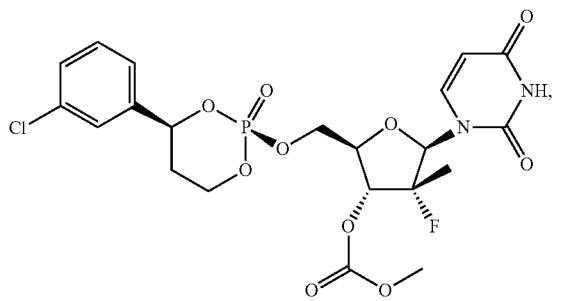
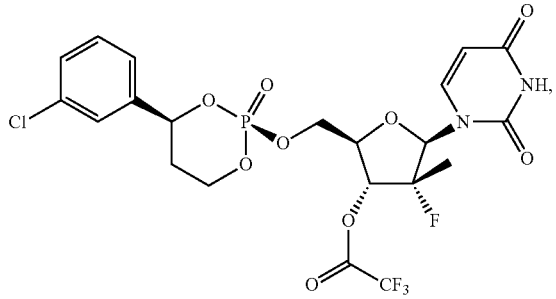

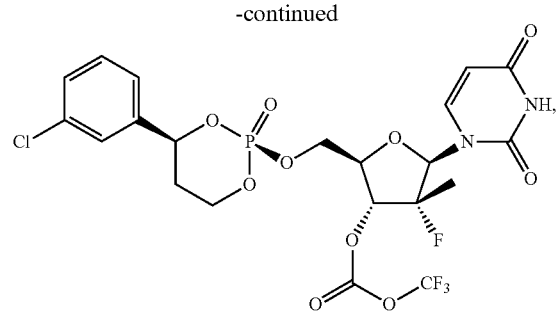
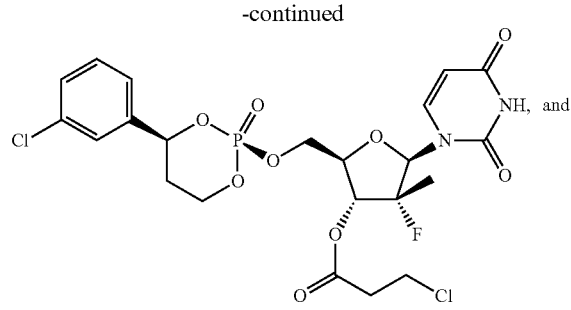
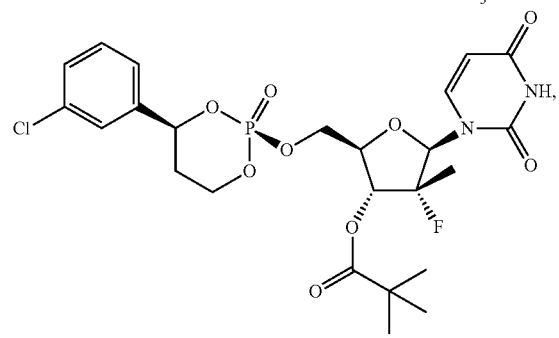
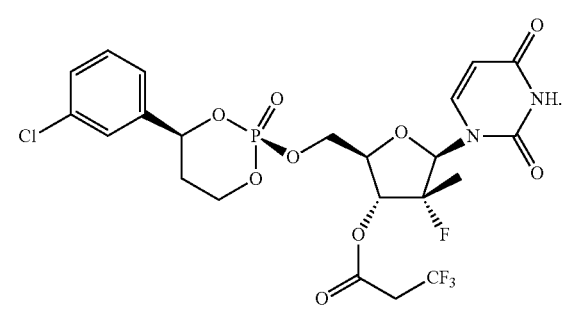
or a pharmaceutically acceptable salt thereof.
* * * * *

UNITED STATES PATENT AND TRADEMARK OFFICE
CERTIFICATE OF CORRECTION

PATENT NO. : 10,000,522 B2
APPLICATION NO. : 15/590813
DATED : June 19, 2018
INVENTOR(S) : Lin Zhi It is certified that error appears in the above-identified patent and that said Letters Patent is hereby corrected as shown below:

On the Title Page

In Column 1 (Notice) at Line 3, After "0 days." delete "days.".

In the Specification

In Column 1 at Line 11 (Approx.), Change "May 29," to --May 28,--.

In Column 11 at Line 45, Change "thereof" to --thereof.--.

In Column 13 at Line 46, After "groups." delete "[0099]".

In Column 14 at Line 15, Change "0" to --O--.

In Column 14 at Line 33, Change "C H" to --C—H--.

In Column 14 at Line 58, Change "terphthalic" to --terephthalic--.

In Column 14 at Line 59, Change "p toluenesulfonic" to --p-toluenesulfonic--.

In Column 15 at Line 54, Change "[1,3,2]dioxaphosphorinane"," to --[1,3,2] dioxaphosphorinane",--.

In Column 18 at Lines 27-28, Change "palmoate," to --pamoate,--.

In Column 18 at Line 29, Change "terphthalate," to --terephthalate,--.

In Column 19 at Line 17, Change "arachid" to --arachis--.

In Column 19 at Line 35, Change "arachid" to --arachis--.

Signed and Sealed this
Second Day of October, 2018

Andrei Iancu
*Director of the United States Patent and Trademark Office*

CERTIFICATE OF CORRECTION (continued)
U.S. Pat. No. 10,000,522 B2

In Column 22 at Line 13 (Approx.), Change "NSSB" to --NS5B--.

In Column 22 at Line 26 (Approx.), Change "NSSA" to --NS5A--.

In Column 23 at Lines 3-12 (Approx.), Change " 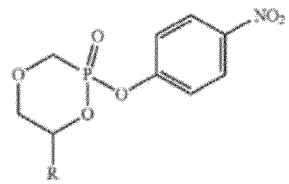 " to -- 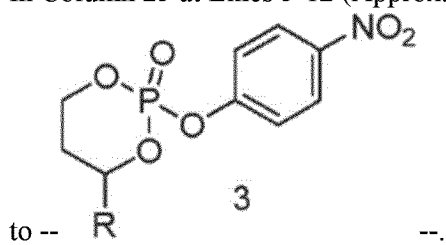 --.

In Column 23 at Lines 28-37 (Approx.), Change " 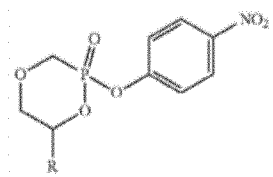 " to -- 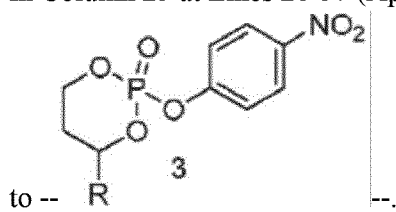 --.

In Column 24 at Lines 6-23 (Approx.), Change " 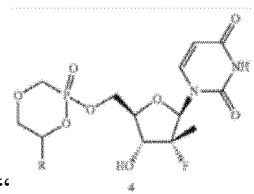 " to -- 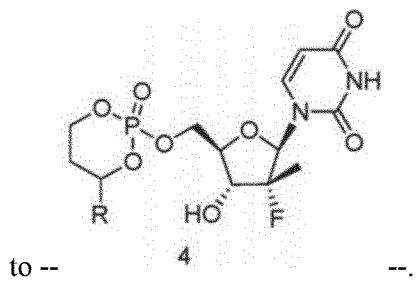 --.

In Column 24 at Lines 33-44 (Approx.), Change " 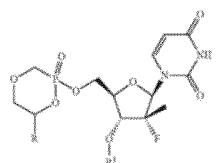 "
to -- 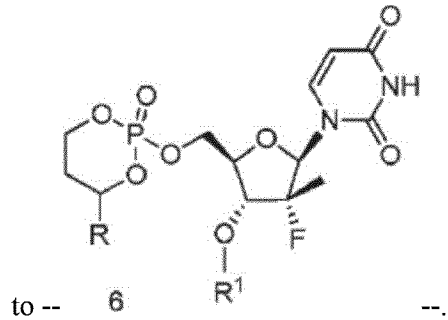 --.
In Column 32 at Line 41, Change "trifluoromethoxycarbonyloxy 3(R)-" to --trifluoromethoxycarbonyloxy-3(R)- --.
In the Claims
In Column 37 at Line 30 (Approx.), In Claim 1, change "$C_1$-C $_8$" to --$C_1$-$C_8$--.
In Column 38 at Lines 63-67 (Approx.), In Claim 7, change " 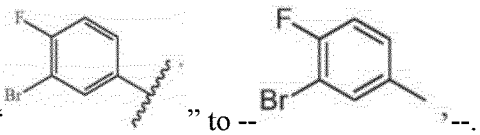 --.